United States Patent
Vola et al.

(10) Patent No.: US 9,968,453 B2
(45) Date of Patent: May 15, 2018

(54) DEVICE FOR CARRYING OUT A TRANSAPICAL MITRAL VALVE ANNULOPLASTY

(71) Applicants: Marco Vola, Saint-Priest-en-Jarez (FR); Bernard Pain, Monistrol-sur-Loire (FR)

(72) Inventors: Marco Vola, Saint-Priest-en-Jarez (FR); Bernard Pain, Monistrol-sur-Loire (FR)

( * ) Notice: Subject to any disclaimer, the term of this patent is extended or adjusted under 35 U.S.C. 154(b) by 233 days.

(21) Appl. No.: 14/778,868

(22) PCT Filed: Mar. 18, 2014

(86) PCT No.: PCT/FR2014/050627
§ 371 (c)(1),
(2) Date: Sep. 21, 2015

(87) PCT Pub. No.: WO2014/147336
PCT Pub. Date: Sep. 25, 2014

(65) Prior Publication Data
US 2016/0045315 A1    Feb. 18, 2016

(30) Foreign Application Priority Data
Mar. 20, 2013 (FR) ...................... 13 52478

(51) Int. Cl.
*A61F 2/24* (2006.01)
*A61B 17/04* (2006.01)
(Continued)

(52) U.S. Cl.
CPC ........ *A61F 2/2466* (2013.01); *A61B 17/0469* (2013.01); *A61B 17/0482* (2013.01);
(Continued)

(58) Field of Classification Search
CPC .............. A61B 17/06061; A61B 17/28; A61B 17/1606; A61B 17/0482; A61B 17/0469;
(Continued)

(56) References Cited

U.S. PATENT DOCUMENTS

| 5,201,880 A * | 4/1993 | Wright .................. A61F 2/2448 623/2.37 |
| 2007/0078514 A1 * | 4/2007 | Ryan .................. A61B 17/0469 623/2.37 |

(Continued)

FOREIGN PATENT DOCUMENTS

WO    2008048626 A2    4/2008

*Primary Examiner* — Jocelin Tanner
(74) *Attorney, Agent, or Firm* — Forge IP, PLLC

(57) ABSTRACT

The device is intended to be positioned in a sealed introducer arranged in the thoracic cavity between two ribs in order to penetrate into the left ventricle, passing through the apex of the heart. According to the invention, the device includes a body having a handle and at least one control member capable of acting on an assembly for installing and securing a braid to the mitral annulus by means of suturing elements, the assembly has a mechanism capable of enabling the extraction of a suture through the mitral valve while also being capable of enclosing the braid and becoming anchored to the periphery of the mitral annulus under the clamping effect of the suture, exerting two opposing pressure-bearing forces.

14 Claims, 14 Drawing Sheets

(51) Int. Cl.
*A61B 17/068* (2006.01)
*A61B 17/064* (2006.01)

(52) U.S. Cl.
CPC .......... *A61B 17/068* (2013.01); *A61F 2/2445* (2013.01); *A61B 2017/0488* (2013.01); *A61B 2017/0498* (2013.01); *A61B 2017/0649* (2013.01)

(58) Field of Classification Search
CPC .... A61B 2017/2926; A61B 2017/0488; A61B 2017/0498; A61B 2017/0649; A61B 2018/0225
See application file for complete search history.

(56) References Cited

U.S. PATENT DOCUMENTS

| | | | |
|---|---|---|---|
| 2007/0112425 A1* | 5/2007 | Schaller | A61B 17/00234 623/2.37 |
| 2009/0093877 A1* | 4/2009 | Keidar | A61F 2/2448 623/2.11 |
| 2011/0106247 A1 | 5/2011 | Miller et al. | |
| 2012/0123531 A1* | 5/2012 | Tsukashima | A61F 2/2448 623/2.37 |
| 2012/0245604 A1 | 9/2012 | Tegzes | |

\* cited by examiner

DEVICE FOR CARRYING OUT A TRANSAPICAL MITRAL VALVE ANNULOPLASTY

FIELD OF THE INVENTION

The invention relates to a device for carrying out a transapical mitral valve annuloplasty.

BACKGROUND OF THE INVENTION

In other words, the annuloplasty aims to reduce the size of the mitral annulus by shortening the attach of the small valve by means of a kinking, the fulcrum being caught between the commissures. Commissure means a narrowing of the posterior portion perimeter of the mitral annulus by performing thereon kinking with stitches, resulting in a decrease in the antero-posterior and latero-lateral diameter of the mitral valve.

A mitral annuloplasty is performed as correcting means of wich mitral leak mechanism is a dilatation of the mitral annulus (with loss of coaptation of the valvular banks) or, in addition to correcting the leak with another mechanism, (mitral valve prolapse) to increase the coaptation of the posterior mitral valve relative to the anterior mitral valve.

A mitral annuloplasty is a long and tough operation which requires the opening of one of the heart chambers and thoracic cavity with extracorporeal blood circulation.

However, many solutions have been proposed to achieve less invasive annuloplasties, avoiding both a pharmacological cardiac arrest (ischemic) of the heart muscle and extracorporeal circulation. Among known processing devices to perform an annuloplasty, it is possible to use an approach into the left atrium, by retrograde way, that is to say from the femoral artery, or an anterograde approach, that is to say by venous and transeptal way. However, these solutions make laborious to locate the mitral annulus. This results in a relatively large investment of time.

An advantageous solution is the transapical approach, i.e to go directly at the apex of the heart.

Such a solution is described for example in WO 2012/167 095.

Difficulties may also arise for the securing of the prosthetic implant at the native mitral annulus. For example, the securing of the mitral annulus can be done either by self-screwing on the shaft (U.S. 2011/010 6247), or by binding the native mitral annulus to a fabric strip with sutures in the form of hooks.

For a sure fixing as such, that is to say the binding of the prosthetic implant at the mitral annulus, the means being implemented enable to only apply a unilateral force so that we can't exclude the risk of leaks caused by poor fixing.

With these systems, many attempts are very often required to achieve a good fixing.

SUMMARY OF THE INVENTION

The aim of the invention is to overcoming these drawbacks in a safe, simple, effective and efficient way.

The problem to be solved by the invention is to facilitate the travel of the device able to perform an annuloplasty along the mitral annulus. This travel arises with a mere transapical retraction/rotation movement using the route to penetrate into the left ventricle through the apex of the heart.

Another object is to facilitate the spacing of the suture stitches of the implant relative to the mitral annulus by performing a simple rotation in either 3D or 2D echocardiography.

Another object is to work without extracorporeal circulation, which requires a sealed device at the body with an elastomeric seal that enables the passage of the movement control members and prevents blood from leaking.

Finally, another object is to improve the implant fixing relative to the mitral annulus by exerting opposite pressure-bearing forces to perform perforation with precision and a passage of an anchoring equipment in a relatively short time and without weakening the adjacent tissue.

To solve such a problem, a device to carry out a transapical mitral valve annuloplasty has been designed and developed, intended to be positioned in a sealed introducer arranged in the thoracic cavity between two ribs in order to penetrate into the left ventricle, passing through the apex of the heart. According to the invention, the device comprises a body equipped with a handle and at least one control member capable of acting on an assembly for installing and securing a braid to the mitral ring by means of suturing elements. Said assembly has means capable of enabling the extraction of a suture through the native mitral annulus while also being capable of enclosing the braid and becoming anchored to the periphery of the mitral annulus under the clamping effect of said suture, exerting two opposing pressure-bearing forces.

To solve the problem of the arrangement of the braid at the mitral annulus, the assembly is constituted by a tubular arm comprising two portions capable of being separated after introduction into the left ventricle, one portion receiving the sutures and being adapted to be brought into contact in the commissure between the mitral valve and the left ventricle walls, the other portion receiving the braid and being capable of passing through the mitral valve and to be positioned at right angles relative to the end of said portion receiving sutures.

To solve the problem of ensuring the spatial positioning of the braid relative to the sutures, the arm portion receiving the braid is made of several elements mounted movable and steerable relative to the portion (4a) which receives the sutures. The free end of the portion receiving the braid is made of two hinged elements. The end of the hinged element is adapted to be positioned substantially perpendicularly to the end of the portion receiving the sutures.

The problem of the introduction of the sutures for the securing of the braid, which is the prosthetic implant, relative to the mitral annulus is solved in that the arm portion receiving the sutures has at its end a needle able to move in translation to protrude from said end, said needle being shaped to allow the engagement, guiding and holding of the suture protruding from said end.

In protruding position of the needle and the suture, and of the suture relative to the needle, said suture leads in an opening in the free end of the arm receiving the braid to form, by considering the nature of the suture material, a loop suitable to enclose a portion of the braid arranged transversely in said opening so that after withdrawal of the needle, the suture being no longer restrained to becoming anchored to the periphery of the mitral annulus.

To solve the problem of enclosing the braid section, said braid is received in two parallel guide channels formed in the thickness of the corresponding portion of the arm so as to form a loop to be enclosed by the suture at the opening of said portion.

To solve the problem of ensuring the deployment of the two end hinged elements of the portion receiving the braid, said elements are coupled in an hinged manner to an element movable in translation connected to an actuating member as a linear slider, so that a movement of the slider in one direction causes the linear movement and the spacing between the two end elements relative to the arm portion receiving the sutures in combination with an arrangement of said arm. The arrangement of said arm is a ramp.

The device is also characterized by the following features, considered in combination:

The end member of the arm portion receiving the braid is connected to a cable connected to a control member actuated by a trigger of the body so as to fold down the end hinged member towards the end of the arm portion receiving the sutures.

The end hinged member of the arm receiving the braid is biased in the alignment position with the other hinged member by a resilient member The hinged end member of the arm receiving the braid cooperates with a stop in the folded-down position.

The means capable of allowing the extraction of a suture to enclose the braid and becoming anchored on the periphery of the mitral annulus consist of a profiled cam for delivering the sutures, a profiled cam for implanting the sutures and a cam for the linear movement of the needle, said cams being connected to a gear system linked to the control trigger and a cable system linked to push members.

Another problem to be solved by the invention is to enable, after installing and securing the braid forming a prosthetic implant relative to the mitral annulus, to reduce the tightening of the valve annulus to avoid any leak risk.

For this purpose, the braid is connected to means suitable to reduce its circumference, after installing and securing on the periphery of the mitral annulus. The means are formed by a pull cord mounted freely in translation in the central core of the braid.

BRIEF DESCRIPTION OF THE DRAWINGS

The invention is described below in more detail with the accompanying figures in which:

FIG. 11: alignment of the various elements of the arm end corresponding to the introduction of the device.

FIG. 12: Opening of the arm after introduction.

FIG. 13: Control of the end member in folded-down position at a portion of the arm receiving the braid.

FIG. 14: Control of the needle.

FIG. 15: Implementation of the loop.

DETAILED DESCRIPTION OF THE INVENTION

Figure 1:
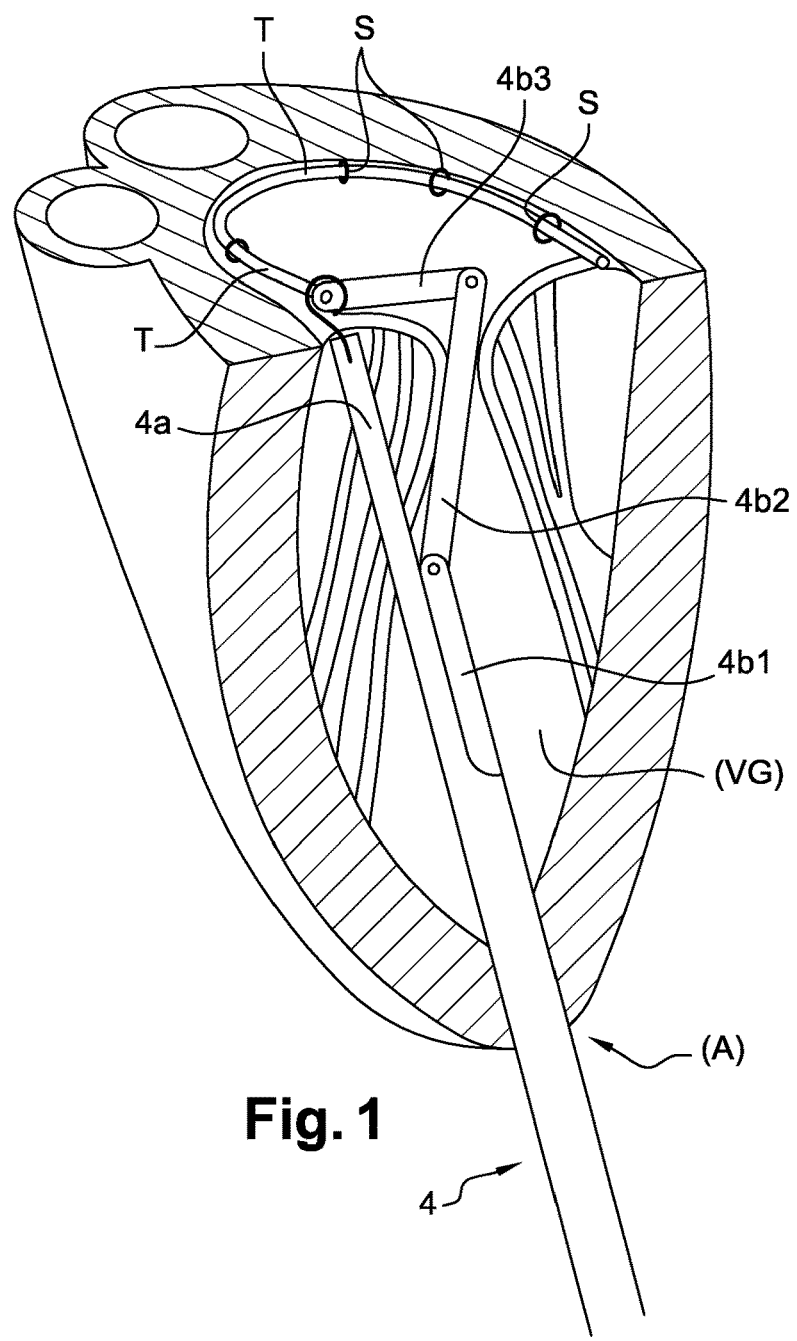
FIG. 1 is a schematic sectional view showing the principle of using the device for carry out an annuloplasty according to the invention.

The device is intended to be positioned in a sealed introducer of any known and suitable type (not shown) disposed in the thoracic cavity between two ribs to get into the left ventricle (LV) through the apex (A) of the heart (FIG. 1).

The device comprises a body (1) having a handle (2) and at least one control member (3), e.g. in the form of a trigger, to act on a assembly for the installing and securing a prosthetic implant as a braid (T) at the mitral annulus by means of suture elements (S).

The assembly consists of a tubular arm (4) comprising two portions (4a) and (4b) adapted to be spaced upon introduction into the left ventricle (LV). One of the portions (4a) receives the sutures (S) and is intended to be placed in contact in the commissure between the mitral valve and the walls of the left ventricle. The other portion (4b) receives the braid (T) and is shaped to be introduced through the mitral valve to be positioned at right angles to the end of the portion (4a) receiving the sutures, as will be indicated in the following description.

The arm portion (4b) which receives the braid is made of several members (4b1), (4b2) (4b3) mounted movable and steerable relative to the portion (4a) of the arm (4).

The two members (4b2) and (4b3) are hinged, the end hinged member (4b3) being suitable to be positioned substantially perpendicularly to the end of the portion (4a) which receives the sutures (S). These two end hinged members (4b2) and (4b3) are also coupled in a hinged manner to an element (4b1) which constitutes a carriage movable in translation, connected to an actuating member in the form of a slider (5).

Figure 11:
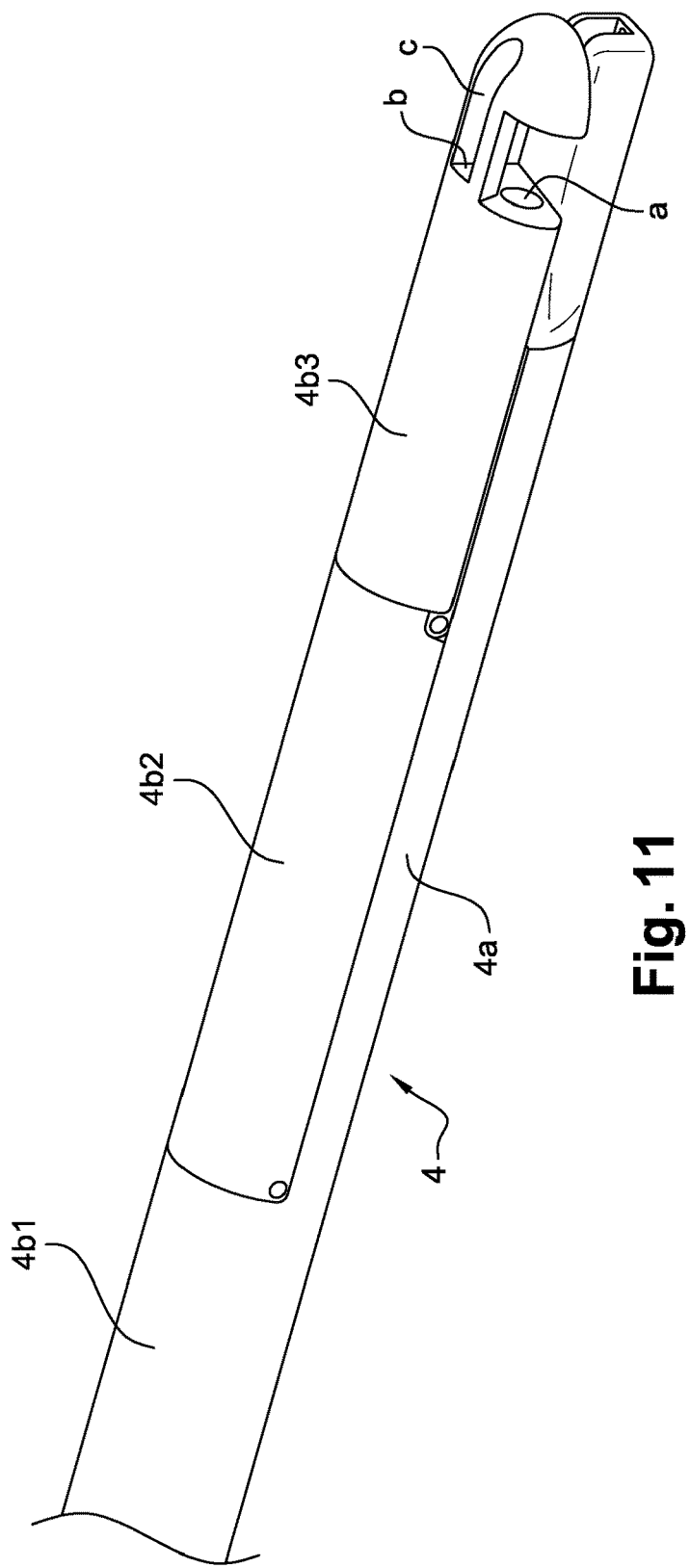
FIGS. 11, 12, 13, 14 and 15 are perspective views of the arm end in different positions, namely.

A linear displacement of the slider (5) in one direction causes linear movement of the movable carriage (4b1) and the spacing of the two end elements (4b2) and (4b3) with respect to the arm (4a) in combination with a ramp (6), for example. And the arm (4b) changes from the position shown in FIG. 11 to the position shown in FIG. 12.

According to another feature, the end member (4b) is connected to a cable (7) linked to a control member as, for example, a cam (8) actuated by the trigger (3), so as to lower said end member (4b3) toward the end of the arm portion (4a) receiving the sutures. In this folded-down position of the end member (4b2), this latter cooperates with a member (9) acting as a stop. A spring (10) returns the members (4b2) and (4b3) in alignment position.

All actuating members pass through a blood-tight seal between the handle and the inside of the heart chamber.

The braid (T) is received slidable in two parallel guide channels (a) and (b) formed in the thickness of the portion (4b) of the arm (4). Both channels (a) and (b) lead in an opening (c) arranged at the free end of the member (4b2) of the arm to allow the braid (T) to form a loop (TA) suitable of being enclosed by a suture, as will be indicated in the following description.

According to another feature, the free end (4a) of the arm (4) comprises a needle (12) movable in translation to protrude from said end. This needle (12) is shaped to allow the engagement, guiding and holding of the suture (S) protruding from said end. It should be noted in this respect that, in known manner, the various sutures are made from a shape memory material so that after being released from said needle, the suture will automatically be deformed to create an anchor buckle.

Figure 14:
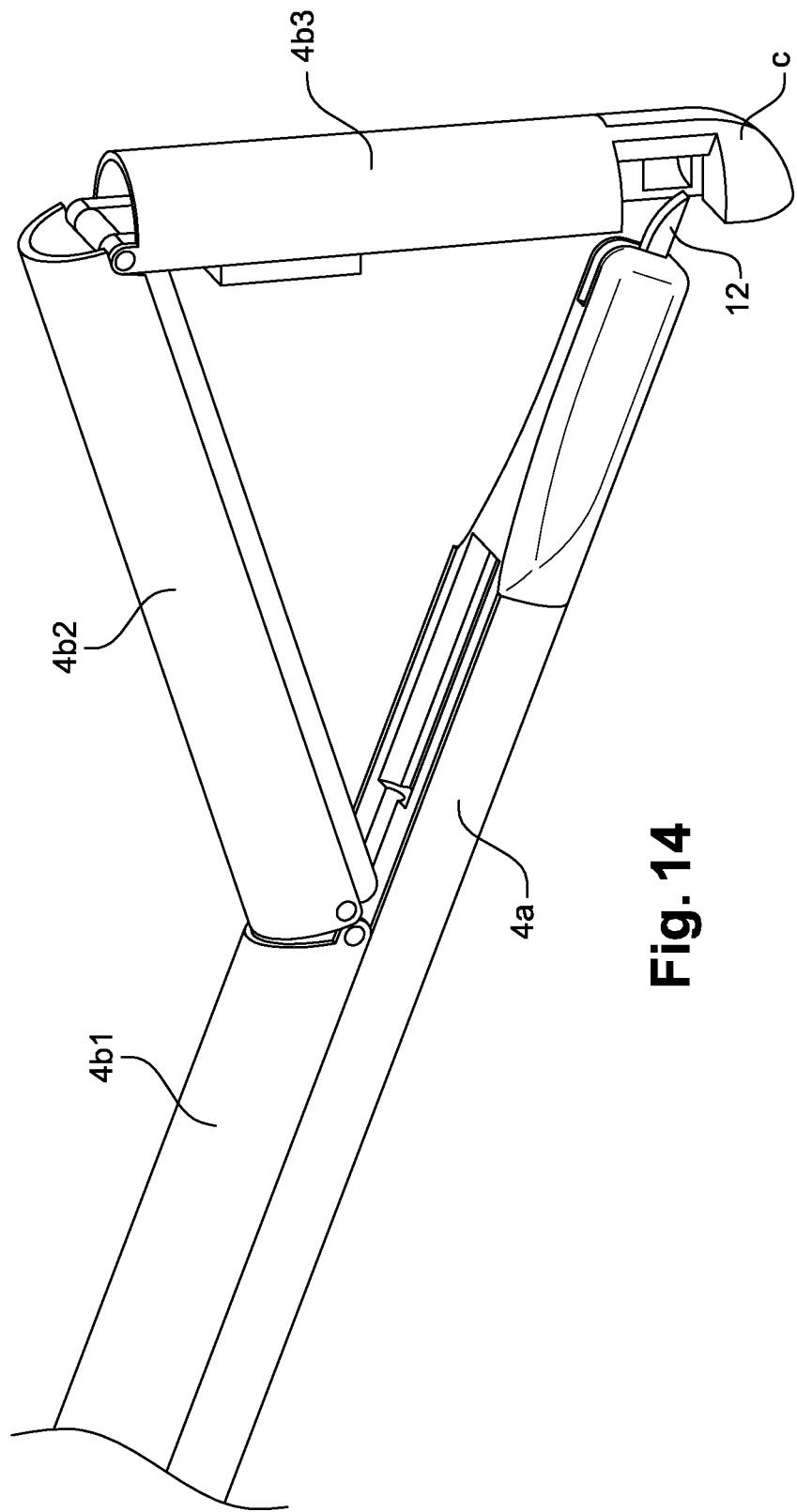
Figure 15:
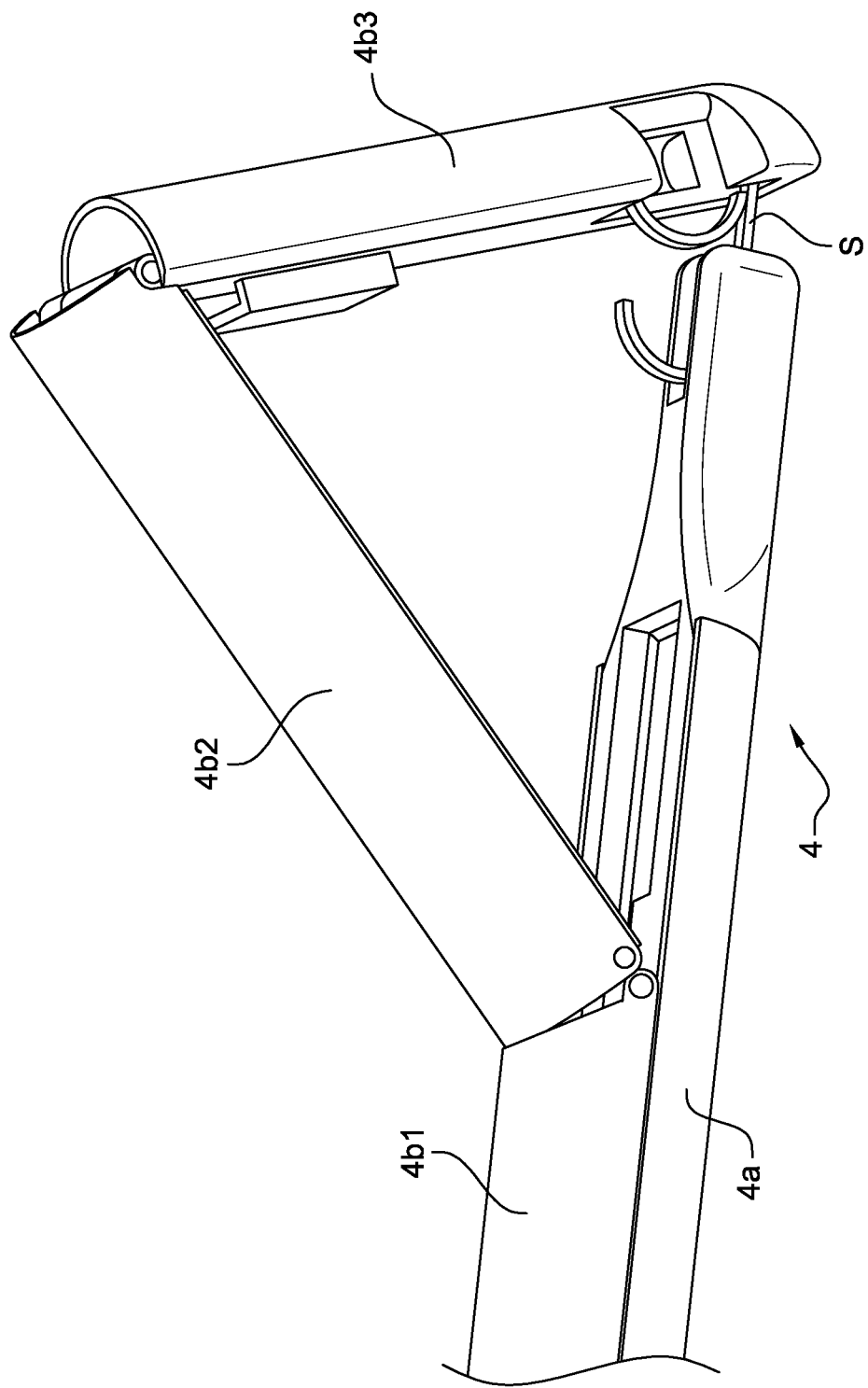
Figure 16:
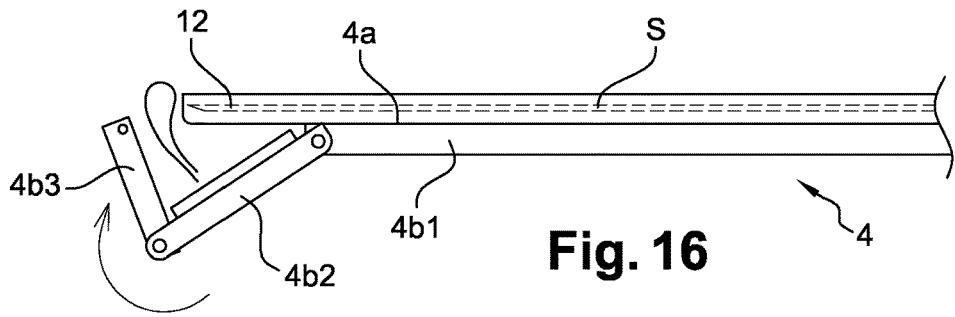
FIGS. 16 to 20 show the implementation principle of the loop relative to the suture.
Figure 17:
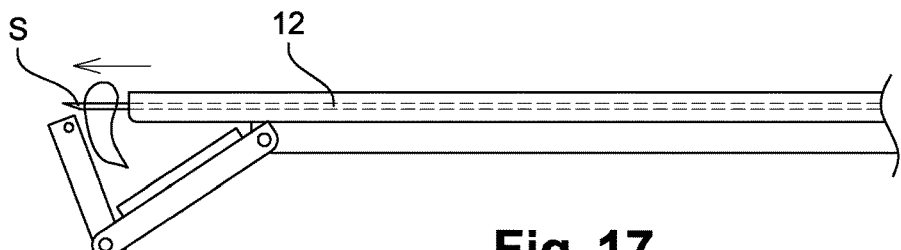
Figure 18:
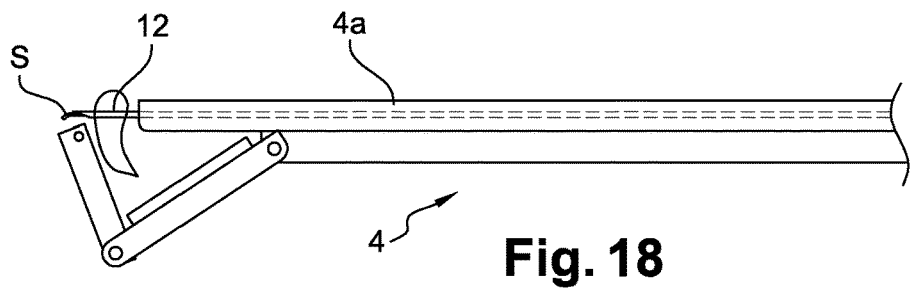
Figure 19:
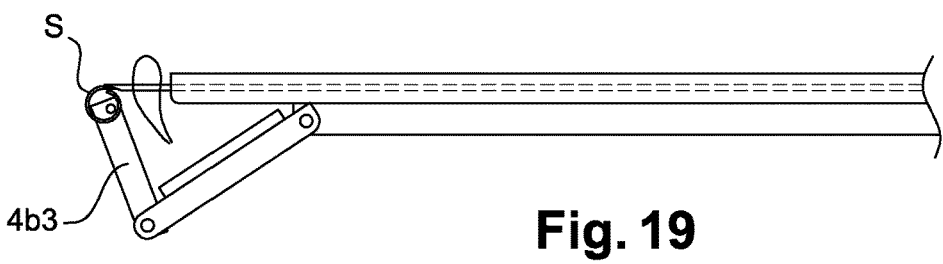
Figure 20:
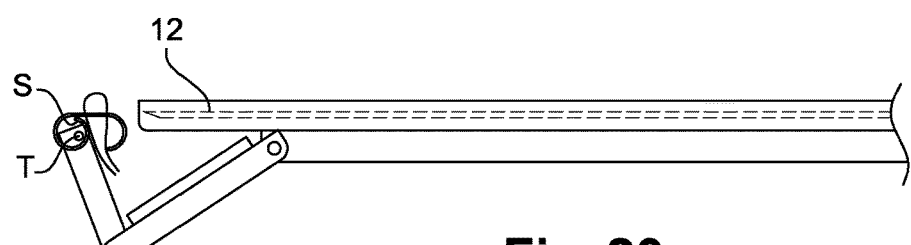

In this protruding position of the needle (12) receiving the suture (FIG. 17) and of the suture relative to the needle (FIG. 18), the suture (S) leads in the opening (c) formed, as indicated above, at the free end of the member (4b2) in which both strands of the suture carry out the loop. After withdrawal of the needle (12) (FIG. 14), by considering the nature of the material of the suture (S), the latter automatically forms an anchoring buckle suitable to enclose the portion of the braid disposed transversely in said opening (c) after being anchored through the tissue of the mitral annulus. For this purpose, to allow the extraction of a suture (S), the apparatus body has a profiled cam (13) for delivering the sutures, a profiled cam (14) for implanting the sutures, and a cam (15) for the linear movement of the needle (12). Said cams are connected to a gear system (17) linked to the control trigger (3) and are connected to a cable system to act on means allowing, as mentioned, to deliver and implant the sutures together with the movement of the needle.

Referring to FIG. 1 of the drawings, the use of the device according to the invention can be describes as follows:

The arm (4) is arranged in an introducer, for example, whose diameter is not greater than 8 mm, disposed in the chest cavity between two ribs, in order to penetrate into the left ventricle (LV) through the apex (A) of the heart. As known, this introducer is intended to allow the passage of the device required for intervention in a fully sealed manner. The arm (4) is then introduced under radiographic control in the introducer thus installed. After introduction into the left ventricle, the two portions (4a) and (4b) are spaced after acting on the slider (5).

The portion (4a) of the arm (4) which receives the shape memory metal sutures (S) is positioned in contact with the commissure between the mitral valve and the walls of the left ventricle (LV).

Figure 12:
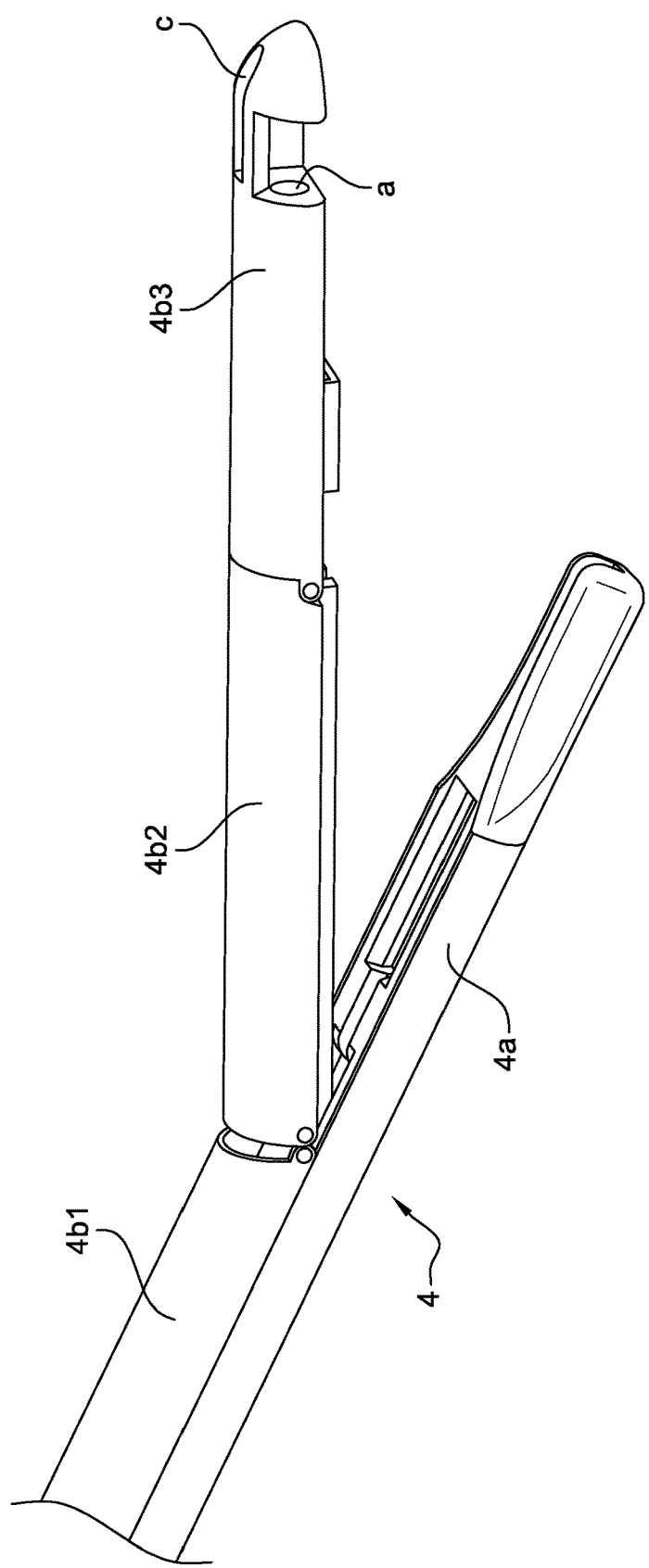
Figure 13:
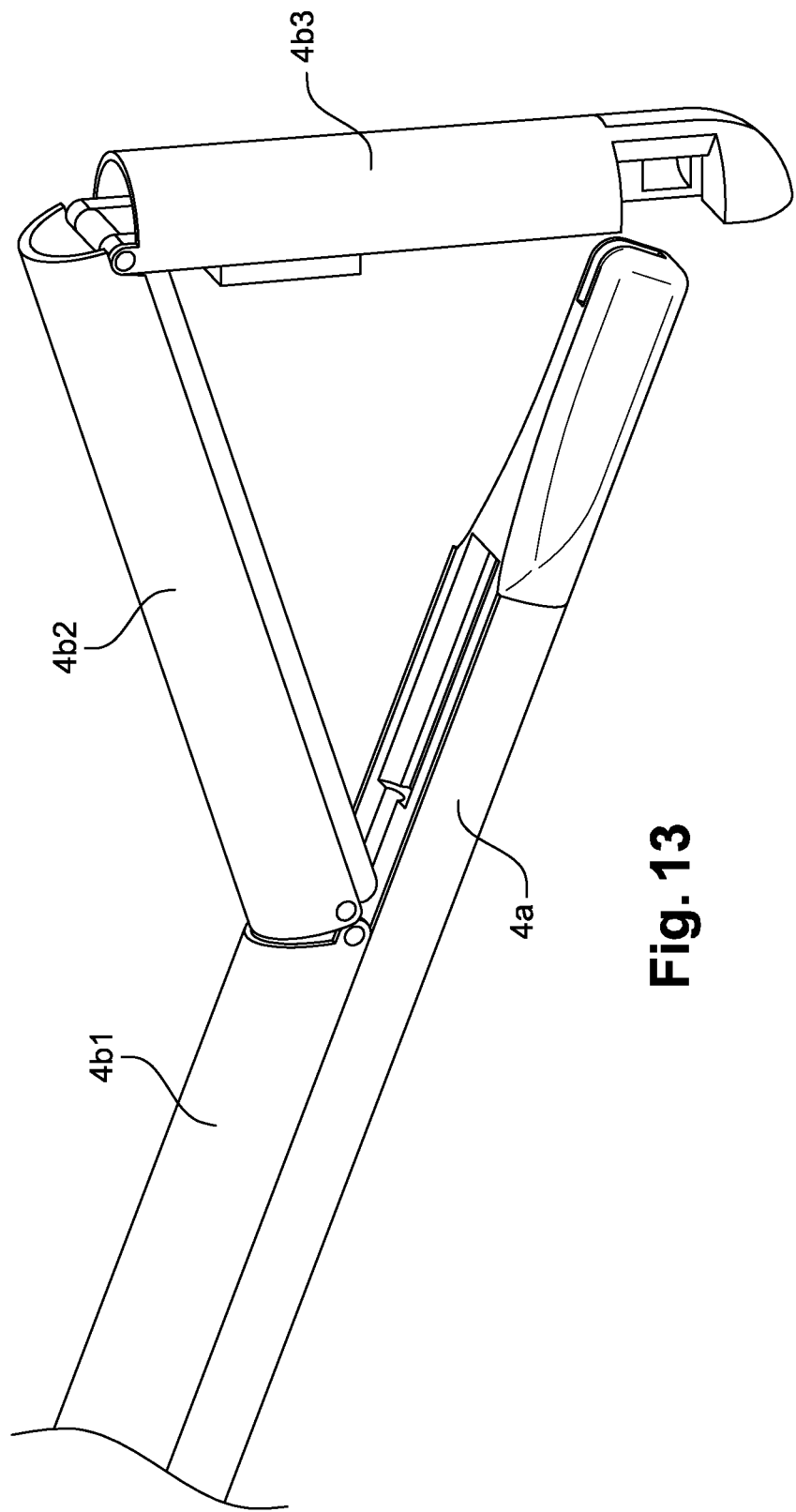

The portion (4b) receiving the braid (T) and which is composed of the various hinged members (4b 1), (4b2), (4b3), passes through the mitral valve in the opened and aligned position of the segments (4b2) and (4b3) (FIG. 12).

Then the trigger is pressed (3) to allow, as indicated above, to fold the end member (4b3) very substantially at right angles with the end of the portion (4a) of the arm (4). Concomitantly it causes the extraction of a suture.

Figure 2:
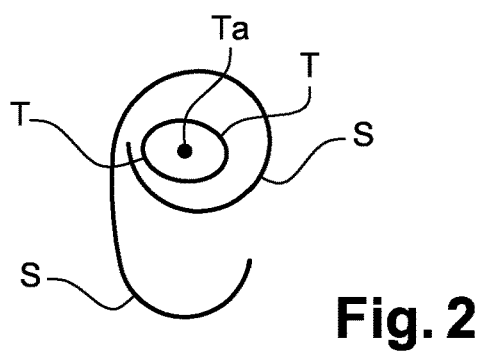
FIG. 2 shows an obtained anchor type
Figure 3:
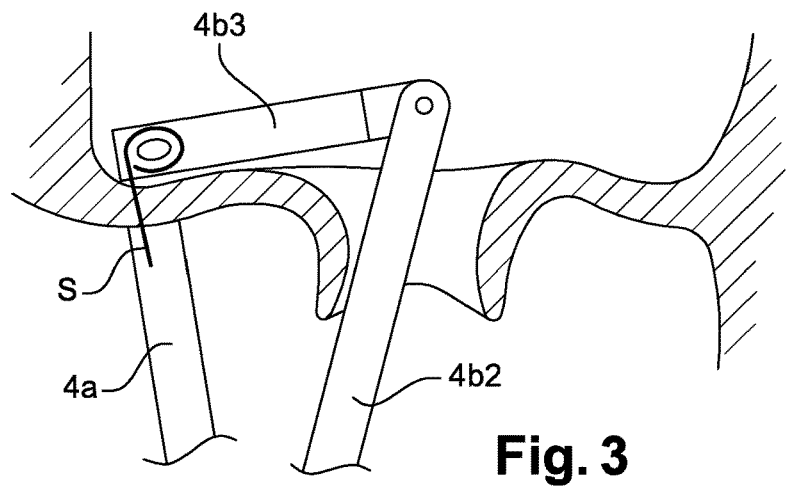
FIG. 3 is a partial schematic sectional view showing the principle of installing a suture relative to the braid forming the implant.
Figure 4:
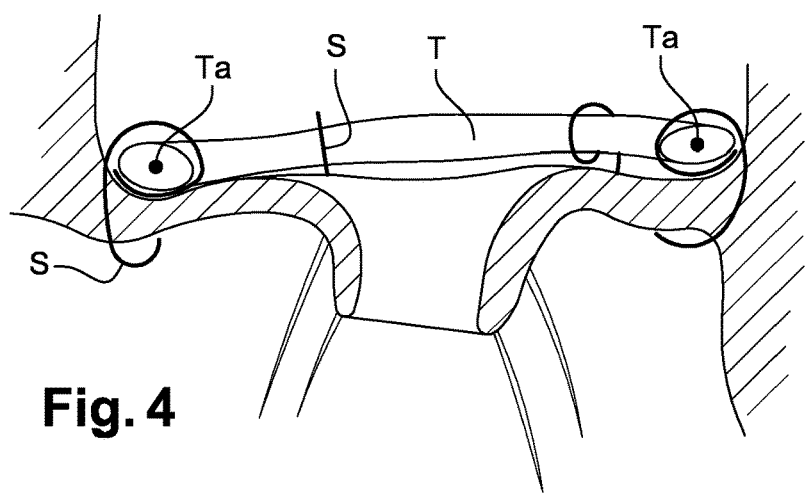
FIG. 4 shows an annuloplasty performed by means of the device according to the invention.
Figure 21:
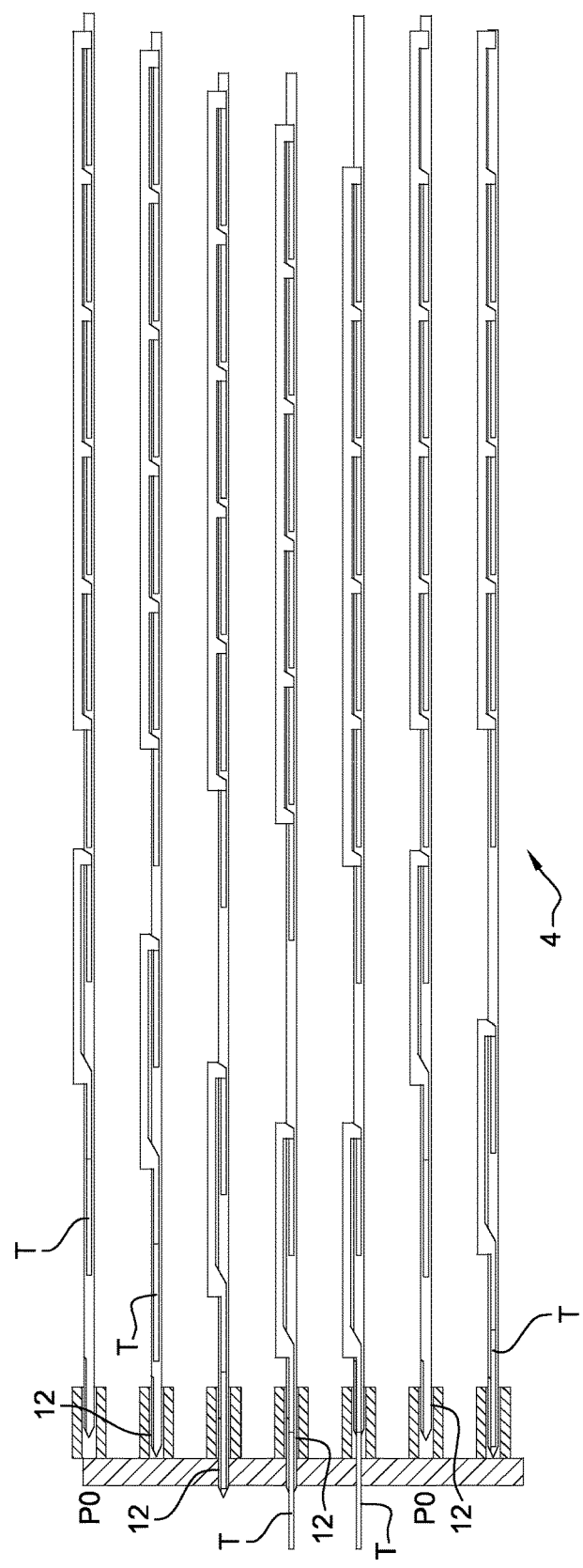
FIG. 21 is a presentation cinematic of the sutures.

Reference is made to FIGS. 16 to 20 and to the cinematic of FIG. 21 showing the layout of the sutures and the carrying out of the anchor buckle. Under the action of a delivering cam, a suture is engaged in the needle (12), which is then moved linearly under the camming to pass through the tissue of the mitral annulus. The suture is then pushed out of the needle (12) to be positioned perpendicularly to the opening (c) of the free end of the member (4b3), that is to say to the portion of the suture forming a loop (TA). After extraction of the needle (12), the suture is completely released in order to constitute, concomitantly, under the effect of the shape memory of its material, an anchor buckle to the periphery of the annulus (FIGS. 2, 4 and 5).

Figure 5:
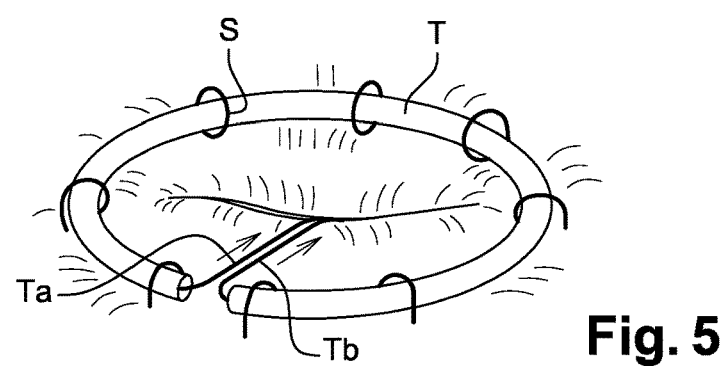
FIG. 5 is a perspective view of the annuloplasty according to FIG. 4.
Figure 6:
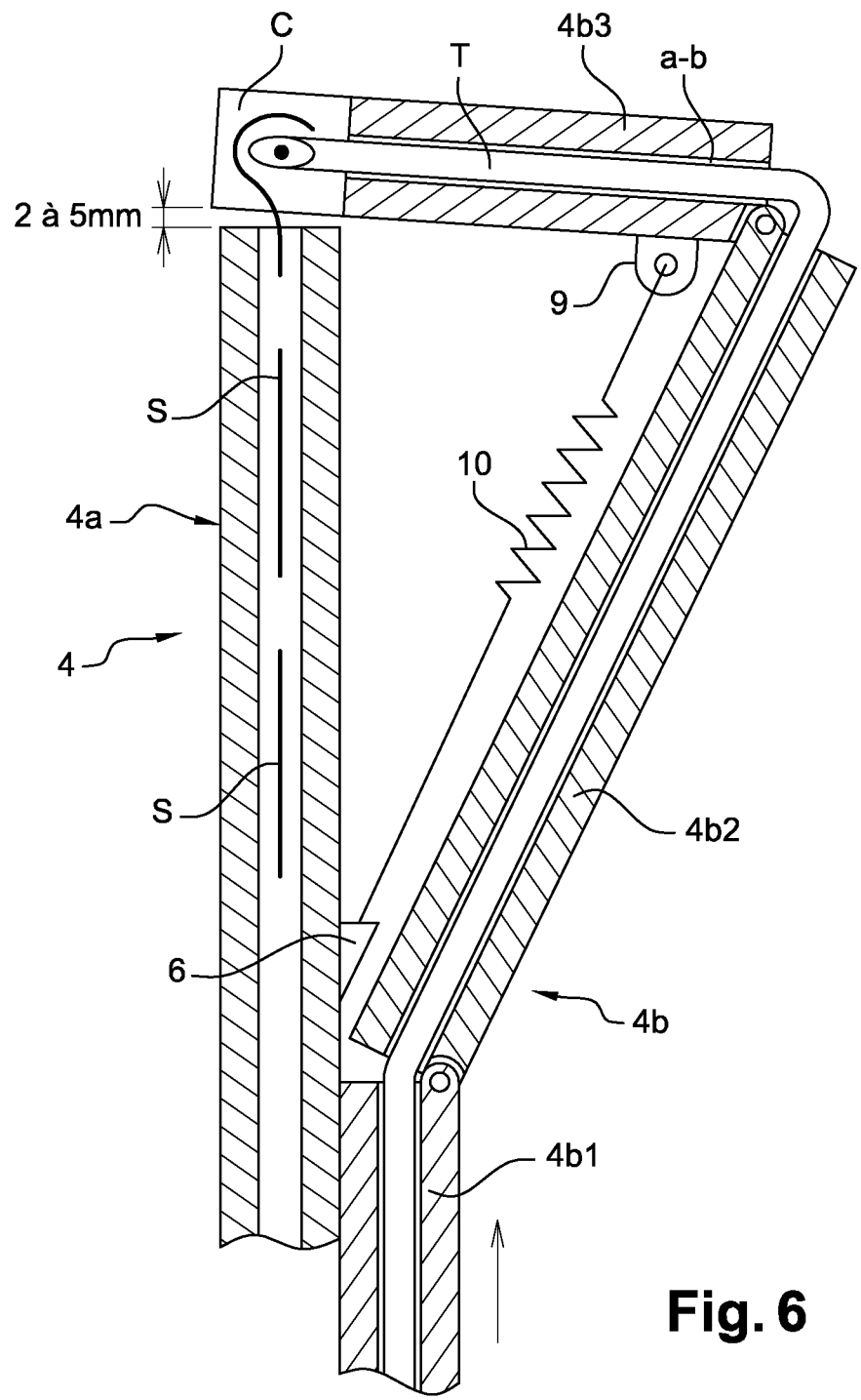
FIG. 6 is a schematic sectional view showing the arm ends of the assembly, for installing metallic sutures in connection with the braid.
Figure 7:
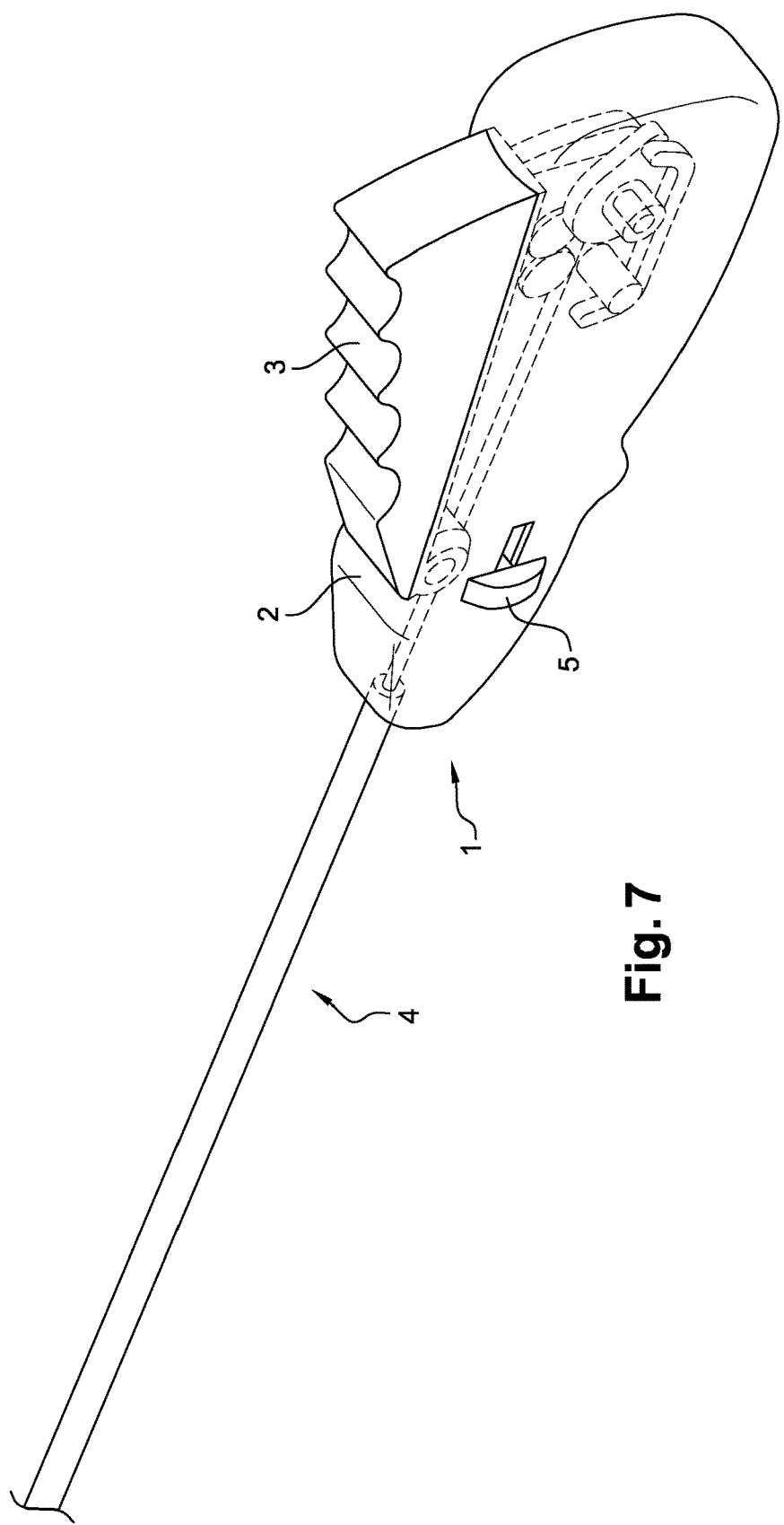
FIG. 7 is a perspective view of one embodiment of the device.
Figure 8:
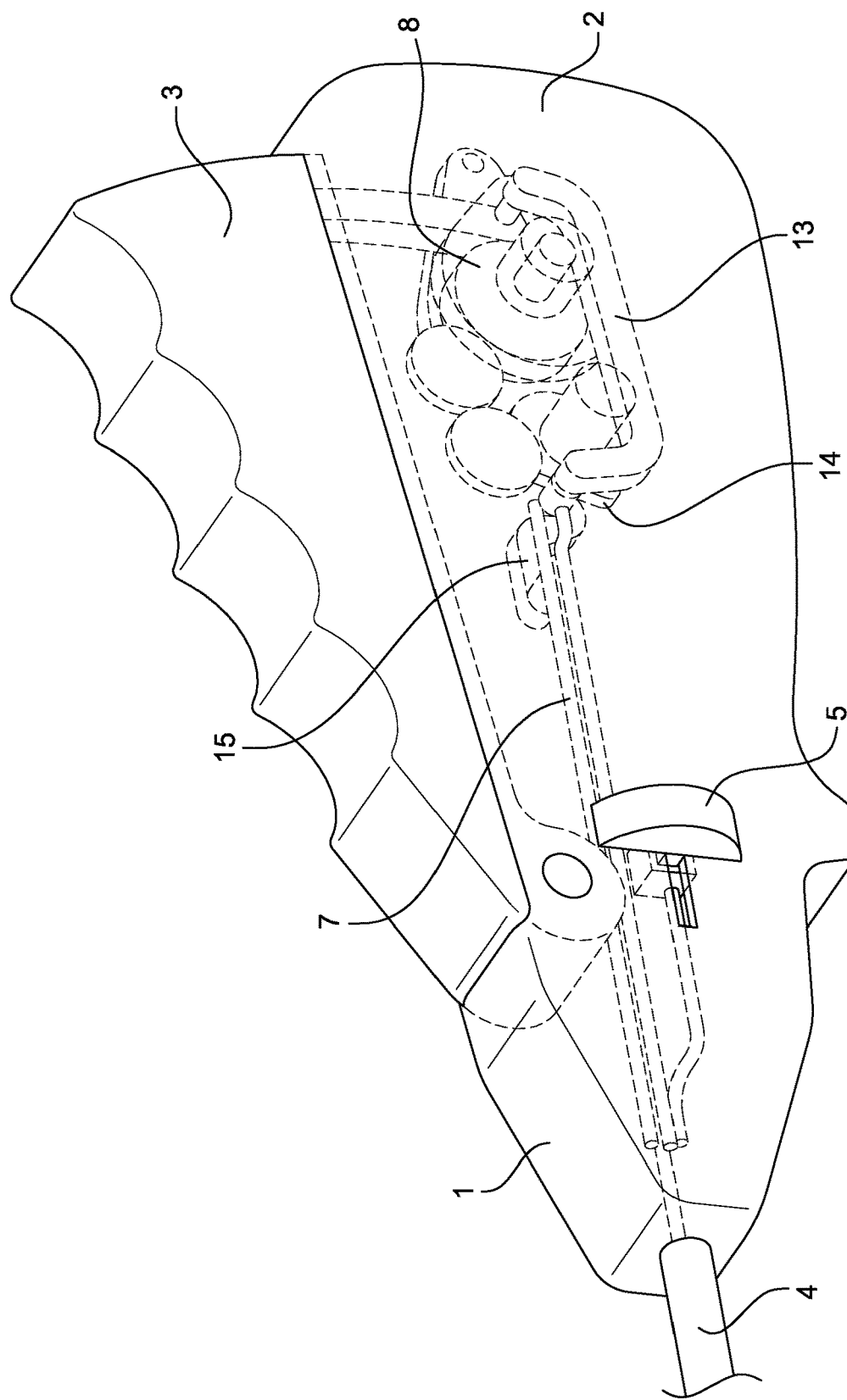
FIGS. 8, 9 and 10 are perspective views of the device at the control handle body showing the control mechanism in different positions to control the component elements of the arm hinged element according to the positioning of a slider (FIGS. 8 and 9) and after acting on the operating handle (FIG. 10)
Figure 9:
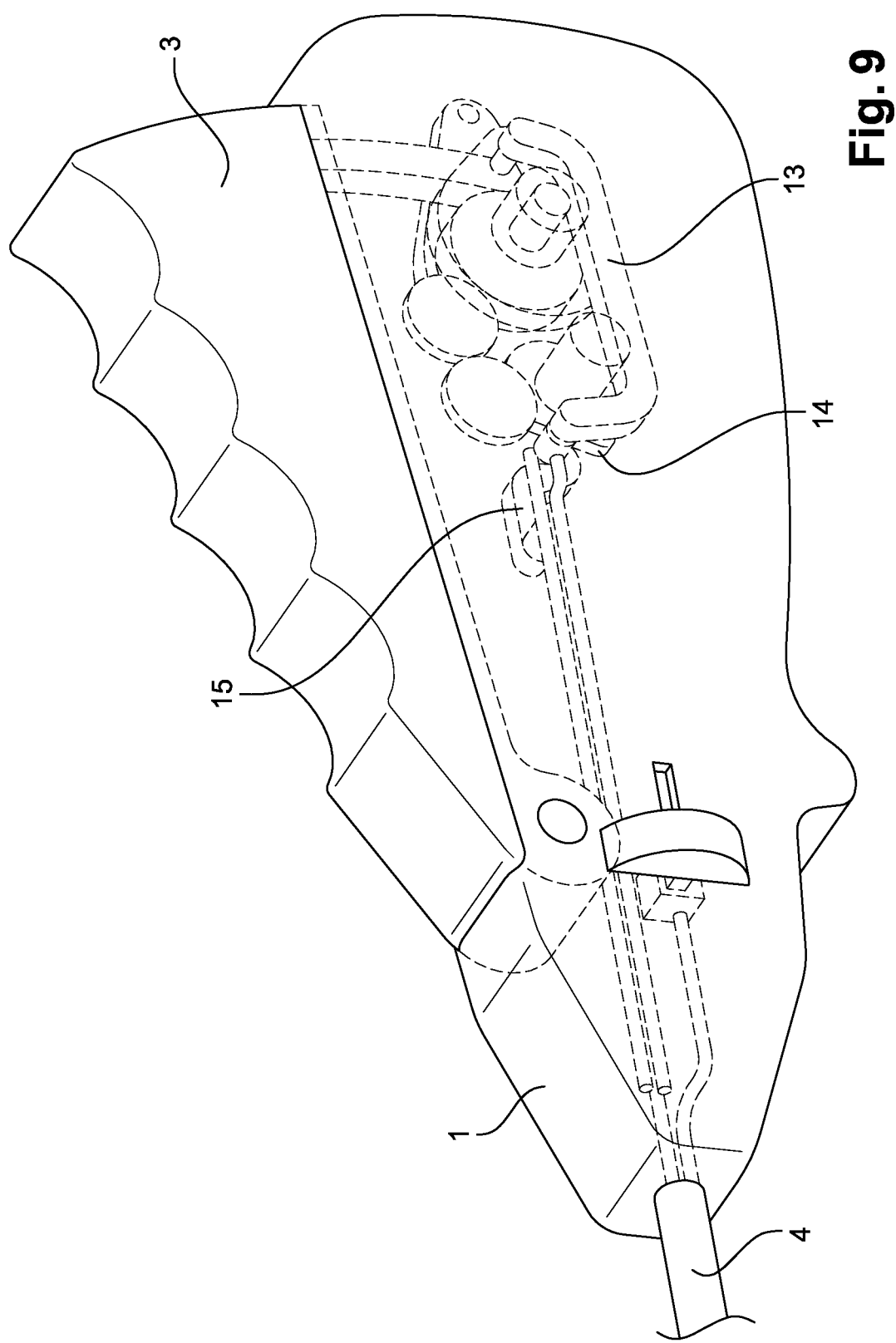
Figure 10:
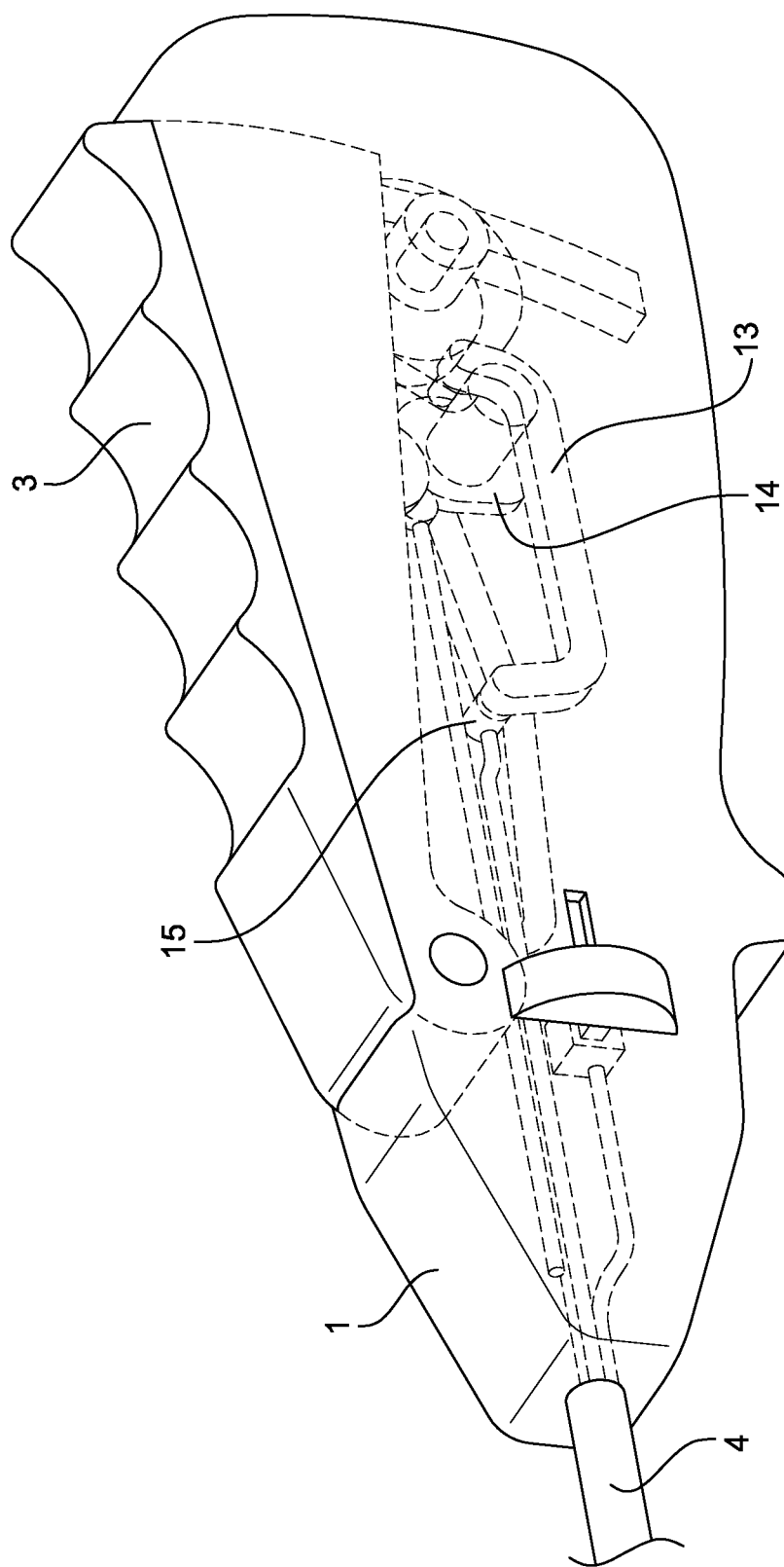

The surgeon repeats several times the process by performing a simple retraction/rotation movement under radiographic control in order to position the required number of sutures on the periphery of the valve annulus (FIG. 5).

According to another important characteristic, the braid (T) capable of forming the prosthetic implant and which can be made of polyester or any other well known material for this type of application is connected to means suitable to reduce its circumference after its installation and securing to the periphery of the mitral annulus, as shown. For example, these means are a pull cord (F) mounted freely in translation and freely sliding into the centrale core of the braid (T) to allow, under a traction effect, ensuring the gathering of the braid and, accordingly, the decreasing of its diameter. These provisions are particularly important to enable after securing of the braid under the specified conditions, to perfectly adapt the diameter of the implant in a fully sealed manner.

For this purpose, the surgeon removes the device and the only both ends of the thread (F) which is the axial core of the braid protrude from the introducer. By exerting a mere radio-controlled traction of the wire the tightening of the annulus of the valve occurs concurrently. After finding the good tightening corresponding to the correct diameter, the wire can be crimped by means of a node or a clip, and then cut.

The features of the device according to the invention provide many advantages over the existing solutions. With the transapical approach from the apex, the operator can easily steer the device to change the angle and the direction of its location or rearward movement. With a 2D ultrasound cutting of the atrioventricular junction, it is possible to visualize the desired isolation of the device on the small mitral valve on the ventricular side. The installation is guided by the tissue anatomy and resistance that the operator feels in the abutment position of the arm end (4). In this regard, we note that the end of arm is bevelled and rounded to travel between the ropes of the mitral system and isolate itself in the dihedral angle at the bottom of which are injected the different sutures. We also note that the device can easily travel with a mere retraction/rotation movement by the left ventricular transapical way for installing the various anchor sutures.

We also note that the device enables to apply two opposite pressure-bearing forces to carry out the tissue perforation and the passage of anchor sutures without risk of weakening said tissue by deleting any risk of trial and error. In other words, the tissue of the mitral annulus and adjacent tissues is punctured more efficiently once with optimal holding of suture staples, each time with an 2D or 3D ultrasound control of the cycle of stapling steps.

What is claimed is:

1. A device for carrying out a transapical mitral valve annuloplasty, and adapted to be positioned in a sealed introducer arranged in a thoracic cavity between two ribs in order to penetrate into a left ventricle, passing through an apex of a heart, characterized in that the device comprises a body having a handle, an assembly that installs and secures a braid to a mitral ring with sutures, and at least one control member connected to said assembly enabling the extraction of said sutures through a mitral valve, said assembly comprising first and second portions arranged to anchor the braid to a periphery of a mitral annulus by exerting two opposing pressure-bearing forces with the first and second portions to clamp said sutures, characterized in that the assembly comprises a tubular arm including the first and second portions which can be separated after introduction into the left ventricle, the first portion receiving the sutures and being adapted to be brought into contact in a commisure between the mitral valve and a wall of the left ventricle, the second portion receiving the braid, and being adapted to pass through the mitral valve and to be positioned at right angles relative to an end of the first portion.

2. The device according to claim 1, characterized in that the second portion is made of several members mounted movable and steerable relative to the first portion.

3. The device according to claim 2, characterized in that an end of the second portion is made of first and second hinged elements, and the first hinged element can be positioned substantially perpendicularly to the end of the first portion.

4. The device according to claim 1, characterized in that the first portion has, at its end, a needle mounted movable in translation to protrude from said end, said needle being shaped to allow engagement, guiding and holding of a suture by protruding from said end.

5. The device according to claim 4, characterized in that said suture is adapted to lead in an opening in an end of the second portion to form a loop suitable to enclose a portion of the braid arranged transversely in said opening after removal of the needle, the suture being no longer restrained to becoming anchored to the periphery of the mitral annulus.

6. The device according to claim 5, characterized in that the braid is received in two parallel guide channels formed in the second portion, so as to form a loop to be enclosed by the suture at the opening of said second portion.

7. The device according to claim 1, characterized in that first and second hinged elements of the second portion are coupled in a hinged manner to an element movable in translation connected to an actuating member as a linear slider, so that a movement of the slider in one direction causes linear movement of and spacing between the two hinged elements relative to the first portion in combination with an arrangement of said first portion.

8. The device according to claim 7, characterized in that said first portion comprises a ramp.

9. The device according to claim 1, characterized in that an end hinged member of the second portion is connected to a cable linked to a transmission member actuated by the at least one control member of the body, so as to lower the end hinged member towards the end of the first portion.

10. The device according to claim 1, characterized in that an end hinged member of the second portion is biased in a position aligned with a second hinged member by a resilient member.

11. The device according to claim 10, characterized in that the end hinged member of the second portion cooperates with a stop in a folded-down position.

12. The device according to claim 1, characterized in that the assembly includes a profiled cam for delivering the sutures, a profiled cam for implanting the sutures and a cam for linear movement of a needle, said cams being connected to a gear system linked to a control trigger and a cable system.

13. The device according to claim 1, characterized in that the braid is adapted to be connected to a circumference of the annulus, after installing and securing on the periphery of the mitral annulus.

14. The device according to claim 13, characterized in that the assembly for reducing a circumference of the braid includes a pull cord mounted freely in translation in a central core of the braid.

\* \* \* \* \*